United States Patent [19]

Harada

[11] 4,375,016

[45] Feb. 22, 1983

[54] VENTED EAR TIP FOR HEARING AID AND ADAPTER COUPLER THEREFORE

[75] Inventor: Mas Harada, Minneapolis, Minn.

[73] Assignee: Qualitone Hearing Aids Inc., Minneapolis, Minn.

[21] Appl. No.: 144,340

[22] Filed: Apr. 28, 1980

[51] Int. Cl.$^{3}$ .......................... H04R 25/02; A61B/7/02

[52] U.S. Cl. ............................. 179/182 R; 179/107 E; 181/135

[58] Field of Search ........................................ 179/107 E, 179/107 FD, 107 H, 107 S, 182 R, 182 A; 181/128–137

[56] References Cited

U.S. PATENT DOCUMENTS

| | | | |
|---|---|---|---|
| 1,830,198 | 11/1931 | French | 181/135 |
| 2,430,229 | 11/1947 | Kelsey | 179/182 R |
| 3,068,954 | 12/1962 | Strzalkowski | 181/23 |
| 3,170,046 | 2/1965 | Leale | 179/107 E |
| 3,368,644 | 2/1968 | Henderson | 179/107 S |
| 3,408,461 | 10/1968 | Langford | 179/107 E |
| 3,470,328 | 9/1969 | Daniels | 179/107 E |
| 3,702,123 | 11/1972 | Macken et al. | 179/107 E |
| 3,934,100 | 1/1976 | Harada | 179/182 R |
| 4,069,400 | 1/1978 | Johanson | 179/107 E |

FOREIGN PATENT DOCUMENTS 606272 8/1948 United Kingdom .

*Primary Examiner*—George G. Stellar
*Attorney, Agent, or Firm*—Schroeder, Siegfried, Vidas, Steffey & Arrett

[57] ABSTRACT

The disclosure is directed to a vent adapter for an ear tip coupling for use with a modular "In The Ear" hearing aid. The ear tip has a bulbous distal tip portion with a sound delivering aperture and a plurality of vent apertures therein. In the assembly, the sound aperture of the ear tip is connected to a sound tube which is part of an adapter which seals the upper portion of the tip. The sound tube projects through the adapter and a separate vent tube also projects through the adapter to provide venting from the other apertures through the ear tip coupler and the vent tube. The vented ear tip and vent adapter can be formed in a number of alternative configurations for varying situations.

6 Claims, 18 Drawing Figures

VENTED EAR TIP FOR HEARING AID AND ADAPTER COUPLER THEREFORE

DESCRIPTION

BACKGROUND OF THE INVENTION

This invention relates to the field of hearing aids, and more particularly to accoustic seals for use with the sound transmitting tube from a modular "In The Ear" hearing aid which is directed into the ear canal.

My prior patent, U.S. Pat. No. 3,934,100, pertains to an acoustic coupling seal for use as an ear tip for insertion within the ear canal. In my prior invention, the tip has a plurality of openings along the axis to form ribbed portions substantially parallel to the axis of the housing, and also includes a disc with a plurality of apertures to permit a direct flow of sound from an external source through the apertures and the openings in the tip to the ear. Because that prior tip permitted sound delivered through the sound tube to escape through the plurality of vent apertures in the disc, a possible problem preventing use of that ear tip for "In The Ear" hearing aids arose through feedback of sound energy from the sound tube through the vent apertures to the microphone of the "In The Ear" type hearing aid.

In another known "In The Ear" hearing aid, a vent tube is provided and cast in the custom molded ear mold. In this type of hearing aid, the venting is provided at a fixed location which may not always be suitable for various wearers of the aid. In other known custom molded hearing aid units, the venting is similarly restricted, and no quickly assembled ear tip coupler can be used as a temporary vented earpiece until a custom ear molded unit has been cast.

SUMMARY OF THE INVENTION

The present invention provides a modular "In The Ear" hearing aid which provides excellent fit and superior venting capabilities without the necessity of using a custom molded construction. The improved modular hearing aid utilizes a soft ear tip which, when used with this new molded vent adapter, forms an ear piece which can be coupled to the sound tube at the output port of an "In The Ear" hearing aid. The ear tip is perforated with an aperture for delivery of sound to the auditory canal and a plurality of other apertures disposed around the sound delivery aperture provide venting from the auditory canal into the interior of the ear tip coupler and through a vent port in the adapter to an external vent. By using the vent adapter and selecting an ear tip from several sizes permits a wearer to be fitted with a hearing aid in one visit and for many persons, avoids the necessity for using a custom molded unit at all.

It is therefore a general object of the present invention to provide an improvement to modular "In The Ear" hearing aids.

It is a more specific object of this invention to provide a novel vent adapter and an improved ear tip coupler for use in combination with a modular "In The Ear" hearing aid to permit fitting of the hearing aid in one visit without the necessity of custom molding the ear tip and the aid to fit the wearer's ear.

BRIEF DESCRIPTION OF THE DRAWINGS

These and other objects and advantages of the invention will be more fully apparent from the following description, made in connection with the accompanying drawings, wherein like reference characters refer to the same or similar parts throughout several views, and in which.

DESCRIPTION OF THE PREFERRED EMBODIMENTS

Figure 1:
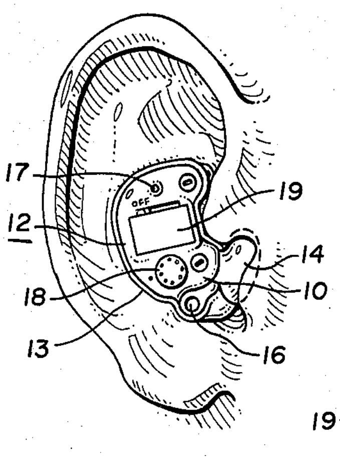
FIG. 1 shows a modular in the ear hearing aid inserted in the ear of a wearer.

As shown in FIG. 1, a hearing aid housing 10 of hearing aid 12 is constructed to fit within the outer ear of the wearer. The hard plastic molded case 10 is enclosed, on at least the surfaces in contact with the ear, in a soft vinyl casing, boot or sleeve 13. The attached ear tip coupler portion 14 projects through the concha and into the auditory canal area. The outer wall of the ear tip coupler portion 14 forms a tight seal at the opening and in the auditory canal.

Figure 2:
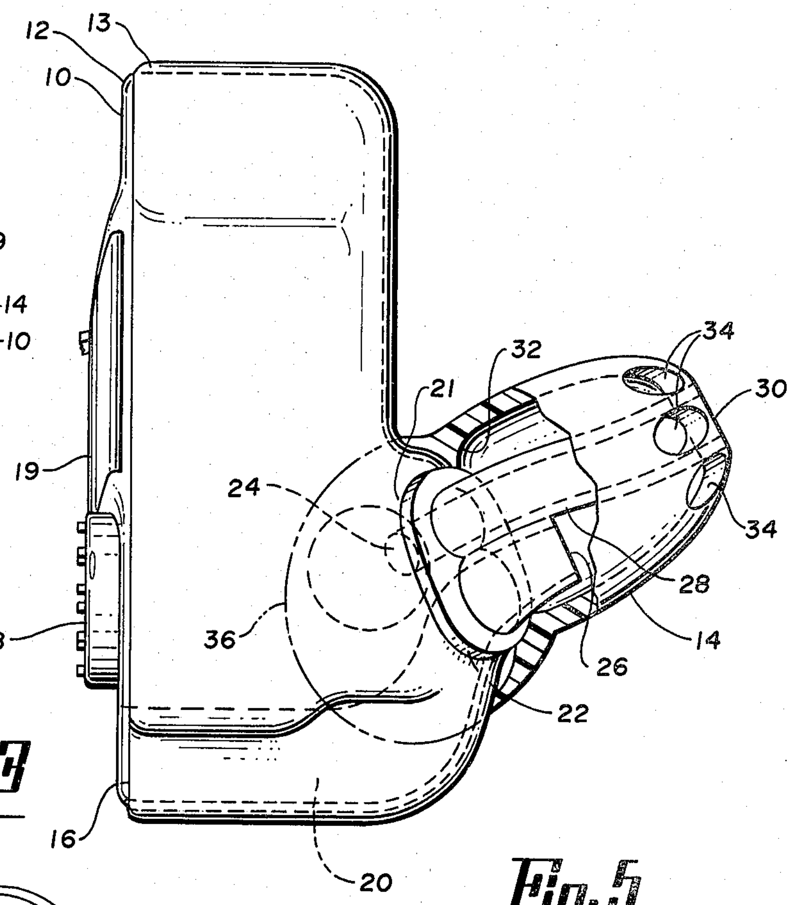
FIG. 2 shows a side view of the hearing aid of FIG. 1.

A sound vent or port 16 is molded into the case boot 13 and as shown in FIG. 2, provides venting from the auditory canal of the wearer to the atmosphere for any excess sound pressure in the canal, and also provides a means for altering the frequency response of the aid by altering the vent diameter and length. The vent 16 shown in the modular "In The Ear" hearing aid of FIGS. 1, 2, 3 and 5 is located at the lower portion of the aid. The microphone input port 17 for the aid shown is located near the top of the housing 10 and well separated from the vent port 16 to prevent feedback of vented sound energy to the input of the hearing aid which would otherwise cause feedback produced oscillation. The volume adjustment control 18 and battery access door 19 are also shown.

Figure 3:
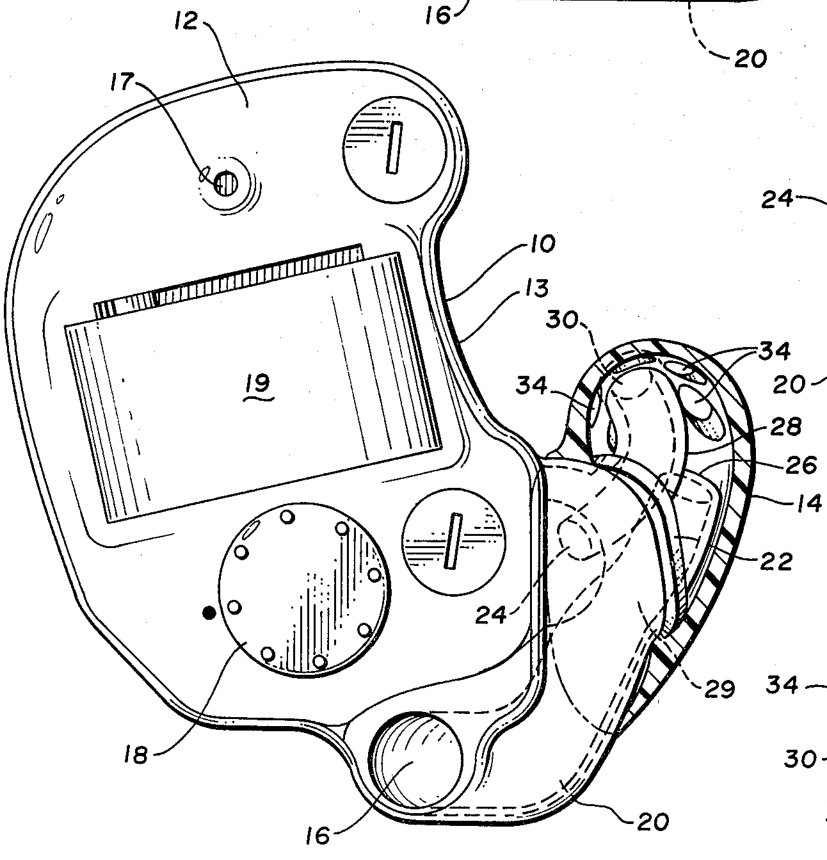
FIG. 3 shows a front view of the hearing aid shown in FIGS. 1 and 2.

As shown in FIGS. 2 and 3, the vent opening or port 16 is the opening of a molded conduit 20, which forms a part of the case boot 13. The vent tube terminates at its other end in a short vent tube 26 which projects into the interior cavity of tip 14. A sealing, coupling or vent adapter 21 is molded as a part of casing, boot or sleeve 13, which has a sealing flange 22 surrounding a pair of openings or ports 24 and 26. Opening 24 is oriented to receive the sound energy from the output transducer of hearing aid 12. A sound tube 28 is connected between the sound port 24 and the sound aperture 30 of the tip portion 14. The sound aperture 30 is positioned to deliver sound energy generally along the axis of the ear canal when inserted.

To provide a snug fit in the wearer's ear, the ear tip portion 14 is formed from a soft material such as vinyl, silicone plastic or foam, which is deformable to assume the shape of the ear canal into which it is inserted. The ear tip is somewhat bulbous toward the distal end in which the sound opening 30 is formed. In the vicinity of the proximal end of the ear tip, there is an inner sealing flange 32 which completely encircles the inner wall of the ear tip. A tight acoustic seal is formed between the flange 22 of adapter 21, and the seal 32 of ear tip 14.

In order to permit the venting of excess sound pressure from the ear canal to the atmosphere, a plurality of apertures 34 are formed in the extreme distal end of the ear tip 14. The apertures are positioned in the vicinity of sound aperture 30 so that they are not blocked after insertion by deformation of the tip 14 by the walls of the ear canal.

The extreme proximal end of the ear tip 14 terminates in a protective skirt or lip 36 to cover the entirety of the adapter 21 and a portion of case boot 13. The function of this projecting proximal portion, boot, or skirt 36 is primarily to assure a clean smooth appearing transition between the ear tip and case boot 13, partially or fully covering the "In The Ear" molded aid.

Figure 4:
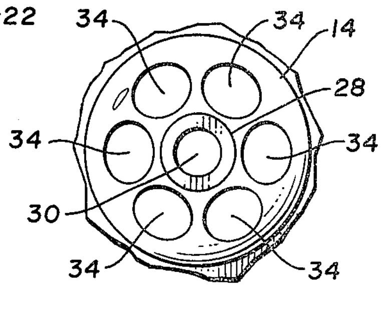
FIG. 4 is a view of the proximal end of the ear tip.

FIG. 4 shows the extreme distal portion of ear tip 14 with the sound aperture 30 circumferentially surrounded by a plurality of vent apertures 34.

Figure 5:
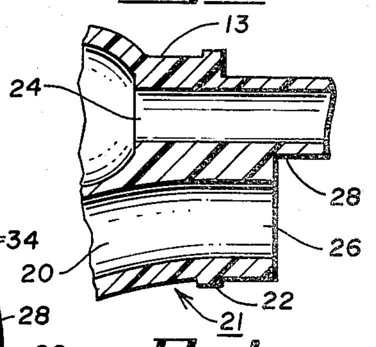
FIG. 5 is a cut away side view of the vent adapter portion of the hearing aid of FIG. 2.

FIG. 5, which shows the detail of the vent adapter portion 21, which is a part of case boot 13 encasing hearing aid housing 10, is a fragmentary cut away view showing the termination of sound tube 28 in the adapter section 21. The flange 22, which fully encircles the adapter to form a seal with the inner annular seal 32 of ear tip 14, is shown in FIG. 2.

Figure 6:
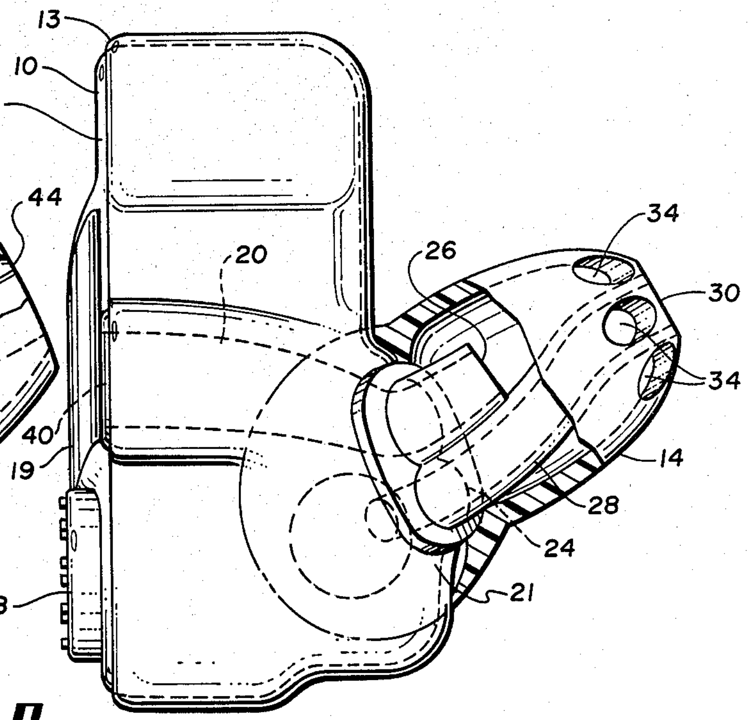
FIG. 6 is a side view of another embodiment of the modular "In The Ear" hearing aid showing the use of mid-line venting.
Figure 7:
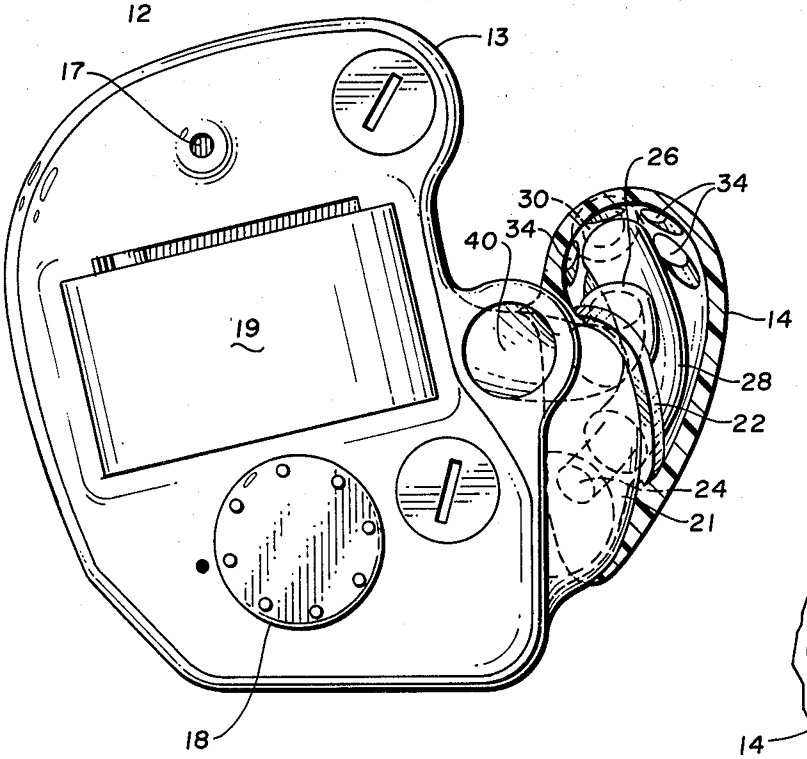
FIG. 7 is a front view of the aid shown in FIG. 6.
Figure 8:
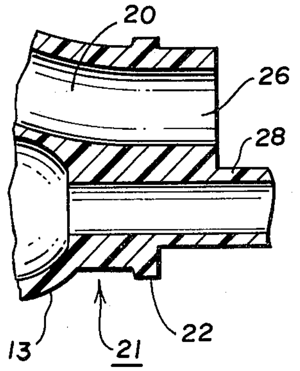
FIG. 8 is a view of the vent adapter portion of the case boot of FIG. 6.

FIGS. 6 and 7 show another embodiment of a modular molded "In The Ear" hearing aid with the ear tip assembly of the present invention. In the embodiment shown in FIGS. 6 and 7, the molded conduit 20 exits from the case housing boot 13 at a vent 40 located at the midline of the unit, rather than at the lower level shown in FIGS. 1 through 3. The other details of the midline vented unit are generally similar to those shown in the lower vented unit, with the exception that the orientation of the vent adapter portion 21 is reversed to move the parallel tube vent opening 26 to the upper position and the sound opening to simplify the orientation of the vent conduit 20 through the case boot housing 13. FIG. 8 shows in detail the adapter portion 21 and its connection to sound tube 28.

Figure 9:
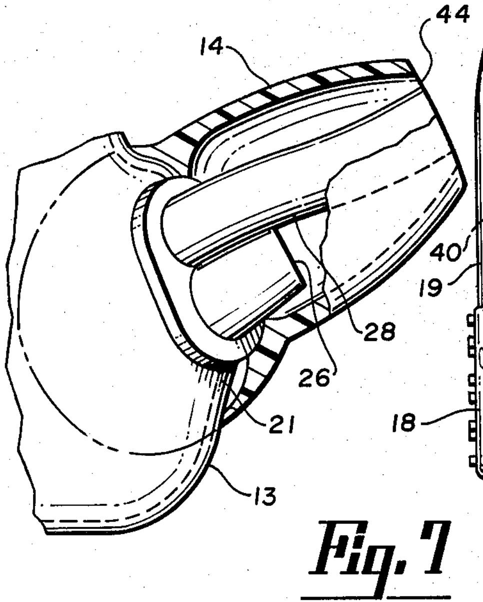
FIG. 9 is a side view of an alternate embodiment of the ear tip coupler with the ear tip cut away.
Figure 10:
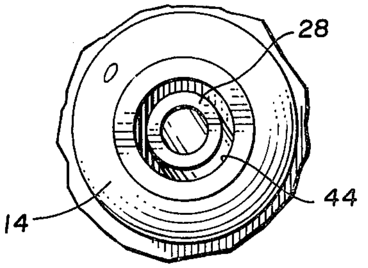
FIG. 10 is an end view of the alternate embodiment ear tip shown in FIG. 9.

FIGS. 9 and 10 illustrate another embodiment of the vented ear tip used in the assembly. In this embodiment, the tip 14 is terminated in a single large aperture opening 44, which is substantially larger in diameter than the outside diameter of sound tube 28. Thus, there is a space between the sound tube 28 and the inner wall of tip 14 to permit venting of excess sound energy from the auditory canal through the vent tip 14 and the parallel tube vent port 26 of adapter 21. The area of aperture 44 exceeds the area of the sound tube 28 by a sufficient amount such that insertion of the tip portion 14 into the auditory canal does not constrict the tip to such a degree that it forms a seal with the distal end of the sound tube 28.

Figure 11:
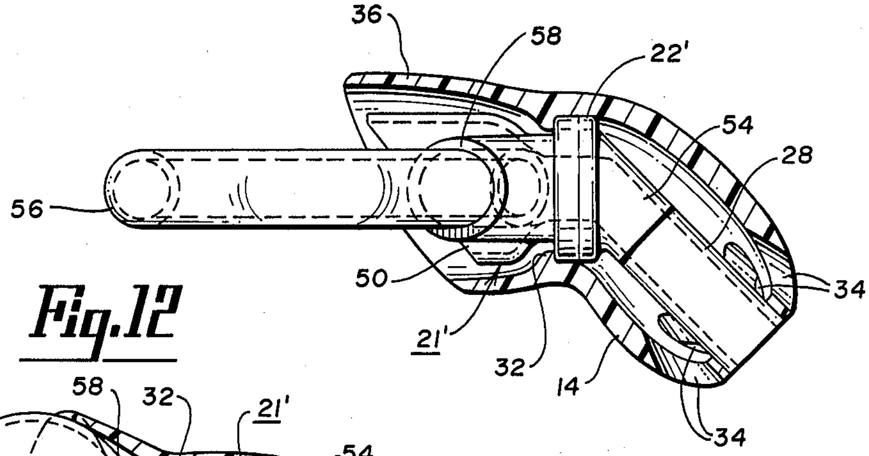
FIG. 11 is a top view of another embodiment of an ear tip vent adapter and coupler assembly with the ear tip shown in cross section.
Figure 12:
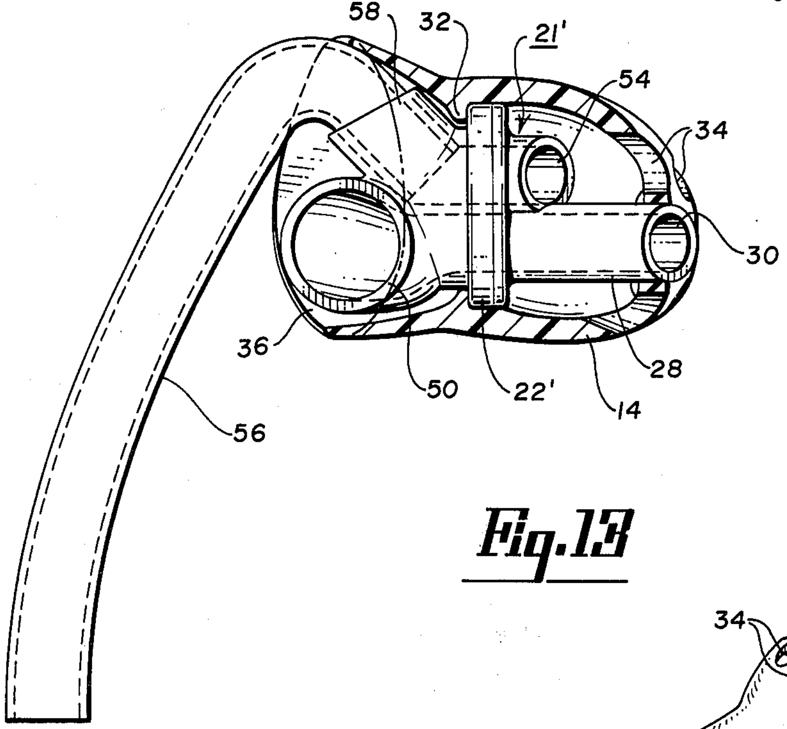
FIG. 12 is a side view of the ear tip assembly of FIG. 11 with the ear tip cut away.
Figure 13:
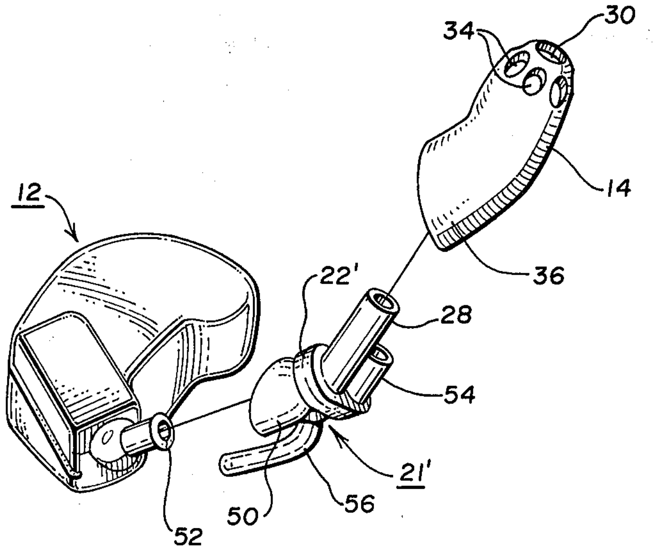
FIG. 13 is an exploded view of a hearing aid and a vent adapter and an ear tip coupler of the embodiment shown in FIGS. 10 and 11.
Figure 16:
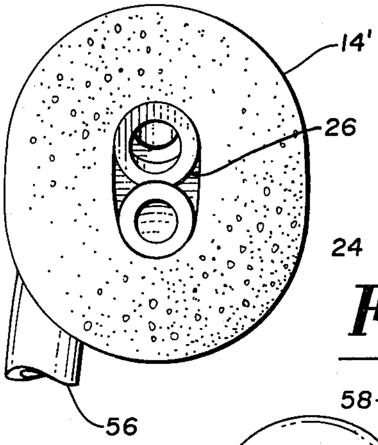
FIG. 16 is an end view of the alternate embodiment ear tip of FIGS. 13 and 14.
Figure 14:
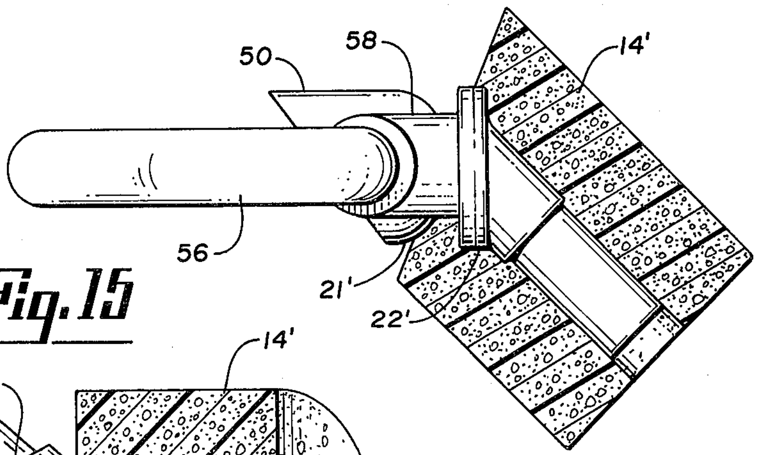
FIG. 14 is a top view of an alternate embodiment of the ear tip assembly with the foam ear tip coupler shown in cross section.
Figure 15:
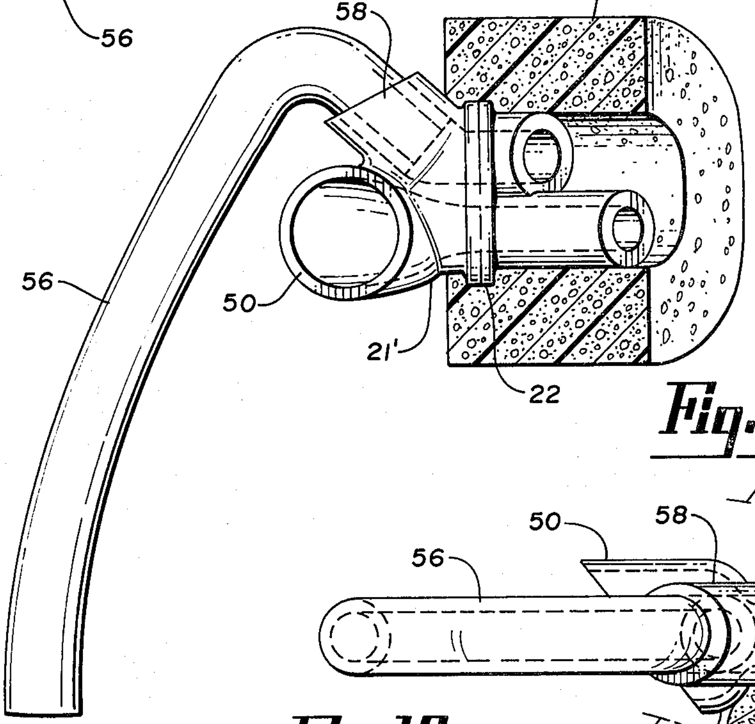
FIG. 15 is a side view of the alternate embodiment of the ear tip of FIG. 13 with the ear tip coupler cut away.

FIGS. 11 through 13 show another embodiment of the vent adapter 21' inserted in the sound output tip portion 12 as shown in FIGS. 2, 3, 4, 6, and 7. In FIGS. 11 through 13, the adapter 21' is a unitary vent adapter functionally similar to the molded vent adapter portion 21 in the case boot 13 shown in FIGS. 1 through 8. A flanged portion 22' forms a seal with the inner annular lip 32 of the flexible tip 14. The skirt of case boot portion 36 of the ear tip covers the proximal end of the vent adapter.

As shown in FIGS. 11, 12, and 13, the adapter 21' is comprised of a sound tube portion 28, which connects to an aperture through the flanged portion 22' and communicates with a flared portion 50, which is constructed and arranged for insertion over the sound delivery tube 52 of a standardized modular "In The Ear" aid 12. A vent tube 54 communicates through an aperture in the flanged portion 22' to a vent conduit 56, which is connected to a projection of the adapter 21' which communicates with the vent aperture through the flanged portion 22'. In order to optimize the performance of the adapter in separating the vented sound energy from the path of the sound energy being delivered to the auditory canal, the adapter 21' has a skewed vent portion 58 which is angled with respect to the axis of the sound delivery tube 28 to facilitate the physical separation of the sound and parallel vent tubes, and permit the venting of the vented excess sound energy at a location physically well removed from the portion of the hearing aid where the microphone port 17 is located.

Figure 17:
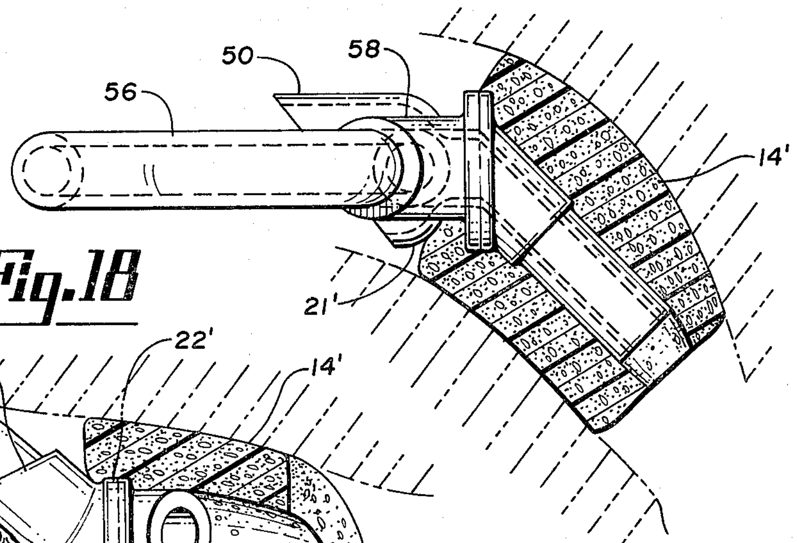
FIGS. 17 and 18 are views of the alternate embodiment ear tip assembly shown in FIGS. 14 and 15 inserted into the ear canal, which is shown in phantom outline.
Figure 18:
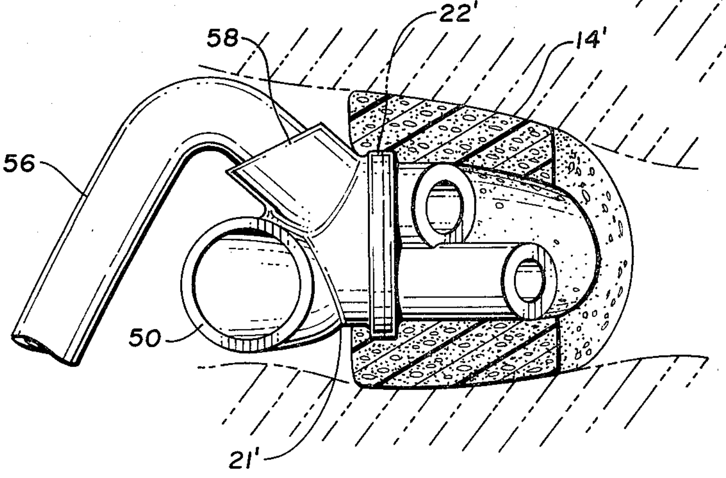

FIGS. 14 through 18 show still another embodiment of tip assembly utilizing the vent adapter 21' and a compressible foam tip portion 14'. In this embodiment, the vent adapter 21' is utilized with a foam ear tip 14' formed from a compressible foam with characteristics as shown in U.S. Pat. No. Re. 29,487. The foam provides a good seal around the body of the adapter 21' and can be compressed to a diameter less than that of the auditory canal. As the foam slowly attempts to return to its original configuration, it seals the auditory canal in a comfortable fashion as shown in FIGS. 17 and 18. The venting is provided through the adapter 21' in the same form as disclosed above. It has been found particularly useful to utilize the foam ear tip 14' in the assembly to accommodate unusually large or irregular auditory canals in certain patients. No adaptation or modification of the adapter 21' itself is necessary to utilize it with the foam tip rather than the vinyl tip 14.

Of course, it will be realized that other changes may be made in the form, details, and arrangement of portion of the parts of the assembly without departing from the scope of the invention, which consists of the structure shown and described herein and set forth in the appended claims.

What is claimed is:

1. An insertable earpiece assembly for delivering sound energy into the ear canal of a wearer, said earpiece assembly comprising:

an elongated hollow housing for insertion into the ear canal of a wearer, said housing having a bulbous distal tip portion having at least one aperture formed therein, said housing is a compressible foam having a normal diameter in excess of the inner diameter of the auditory canal of a wearer and a diameter when compressed slightly less than the inner diameter of the auditory canal of a wearer;

an adapter member for sealing said housing and having a sound opening and a vent opening formed therein; and a sound tube for connecting the sound opening of said adapter member to one of said apertures in said housing, the area of said tube being less than the combined area of said apertures to permit excess sound pressure in the ear canal to be vented through said housing and said vent opening.

2. The invention of claim 1 wherein the bulbous tip portion of said hollow housing has a single aperture with an area substantially greater than the area of said tube to permit venting of excess sound pressure between said housing and said sound tube.

3. An insertable ear tip coupler comprising, in combination:

a soft elongated hollow ear tip for insertion into the ear canal of the wearer, said ear tip having a bulbous distal tip portion with an aperture formed therein and a plurality of smaller apertures formed circumferentially around said aperture, said tip having an inner annular shoulder portion formed near the proximal end of the tip; and a vent adapter constructed and arranged for insertion into said ear tip to form a seal against the inner annular shoulder thereof to seal the proximal end of said ear tip, said adapter including a sound tube connected at one end to said aperture and projecting through said adapter to receive sound energy, said adapter also including a vent opening through said adapter, said vent opening constructed and arranged for coupling to a vent tube to vent excess sound pressure at a location remote from said sound tube.

4. The invention of claim 3 wherein said vent opening of said vent adapter is provided with a vent fitting constructed and arranged to receive a vent tube.

5. An insertable earpiece comprising, in combination:

an elongated generally cylindrical hollow housing with a bulbous tip portion ventilated by a plurality of apertures in a distal end thereof and a flared proximal tip portion with an inner annular shoulder angled to the axis of said housing;

a flanged adapter fitting seated against the inner annular shoulder of said housing to close the proximal end of said housing, said fitting including a sound tube projecting into said housing to communicate with at least one of said apertures in the distal end of said tip portion while more than one of the plurality of said apertures communicates with a chamber in said housing; and a vent tube projecting through said fitting into said chamber to provide a path from the auditory canal through said chamber to the outside, said vent tube portion extending into said housing being shorter than said sound tube and the other end of said vent tube being angled away from the axis of the tube delivering sound to said fitting.

6. An insertable earpiece assembly for delivering sound energy into the ear canal of a wearer, said earpiece assembly comprising:

an elongated hollow housing for insertion into the ear canal of a wearer, said housing having a bulbous distal tip portion having a plurality of smaller vent apertures disposed circumferentially around a central sound opening aperture;

an adapter member for sealing said housing and having a sound opening and a vent opening formed therein; and a sound tube for connecting the sound opening of said adapter member to said central aperture in said housing, the area of said tube being less than the combined area of said vent apertures to permit transmission of sound through said sound tube without interference with said plurality of vent apertures thereby permitting excess sound pressure in the ear canal to be vented through said housing and said vent opening.

* * * * *